US012709723B2

(12) United States Patent
Grimm et al.

(10) Patent No.: US 12,709,723 B2
(45) Date of Patent: Aug. 18, 2026

(54) ADAPTING CONTROL OF A CELL CULTURE IN A PRODUCTION SCALE VESSEL WITH REGARD TO A STARTING MEDIUM

(71) Applicant: Sartorius Stedim Data Analytics AB, Umea (SE)

(72) Inventors: Christian Grimm, Heilbad Heiligenstadt (DE); Stefan Schlack, Göttingen (DE); Johan Trygg, Umea (SE)

(73) Assignee: Sartorius Stedim Data Analytics AB (SE)

( * ) Notice: Subject to any disclaimer, the term of this patent is extended or adjusted under 35 U.S.C. 154(b) by 1112 days.

(21) Appl. No.: 17/781,685

(22) PCT Filed: Nov. 26, 2020

(86) PCT No.: PCT/EP2020/083449

§ 371 (c)(1),
(2) Date: Jun. 1, 2022

(87) PCT Pub. No.: WO2021/110520

PCT Pub. Date: Jun. 10, 2021

(65) Prior Publication Data

US 2023/0002708 A1 Jan. 5, 2023

(30) Foreign Application Priority Data

Dec. 3, 2019 (EP) .................................... 19213037

(51) Int. Cl.
*C12M 1/36* (2006.01)
*G16B 40/20* (2019.01)

(52) U.S. Cl.
CPC .............. *C12M 1/36* (2013.01); *C12M 41/48* (2013.01); *G16B 40/20* (2019.02)

(58) Field of Classification Search
None
See application file for complete search history.

(56) References Cited

U.S. PATENT DOCUMENTS

| | | | |
|---|---|---|---|
| 2009/0143873 | A1 | 6/2009 | Navratil et al. |
| 2015/0353896 | A1 | 12/2015 | Bruninghaus et al. |
| 2019/0219992 | A1 | 7/2019 | Grimm et al. |

FOREIGN PATENT DOCUMENTS

| | | | |
|---|---|---|---|
| CN | 110023482 A | | 7/2019 |
| EP | 3 291 038 A1 | | 3/2018 |
| WO | WO 2018/115161 A1 | | 6/2018 |
| WO | WO 2019/094787 A1 | | 5/2019 |

OTHER PUBLICATIONS

Cunha et al., "An assessment of seed quality and its influence on productivity estimation in an industrial antibiotic fermentation," *Biotechnology and Bioengineering* 78(6): 658-669, Jan. 2002.

International Search Report and Written Opinion, mailed Feb. 18, 2021, issued for International Patent Application No. PCT/EP2020/083449, 11 pages.

Fernando Ayala Solares et al., "Development of an N-1 perfusion medium to intensify seed train operation," *Integrated Continuous Biomanufacturing IV*, 2019.

*Primary Examiner* — G. Steven Vanni
(74) *Attorney, Agent, or Firm* — Klarquist Sparkman, LLP

(57) ABSTRACT

A computer implemented and a system for adapting control of a cell culture in a production-scale vessel with regard to a starting medium are provided. The method comprises providing multiple production-scale process trajectories, receiving a media lot for the cell culture, and sampling first media from the media lot for possible use in the production-scale vessel. The method also comprises starting a seed train using the first media to achieve inoculation of the production-scale vessel, providing a plurality of micro-scale vessels in a process control device, and sampling second media from the media lot for the micro-scale vessels. Cells from the seed train can be introduced into the micro-scale vessels to start cell cultures in each of the micro-scale vessels.

17 Claims, 7 Drawing Sheets

ADAPTING CONTROL OF A CELL CULTURE IN A PRODUCTION SCALE VESSEL WITH REGARD TO A STARTING MEDIUM

CROSS REFERENCE TO RELATED APPLICATIONS

This is the U.S. National Stage of International Application No. PCT/EP2020/083449, filed Nov. 26, 2020, which was published in English under PCT Article 21(2), which in turn claims the benefit of European Patent Application No. 19 213 037.5, filed Dec. 3, 2019. The prior applications are incorporated herein by reference in their entirety.

The present disclosure relates to chemical, pharmaceutical, biopharmaceutical and/or biological process control. More particularly, disclosed aspects relate to adapting control of a cell culture in a production-scale vessel with regard to a starting medium.

Cell culture media can be a significant source of variability to biopharmaceutical manufacturing processes and can detrimentally affect cellular growth, viability, and specific productivity, or alter the quality profile of a resulting product (e.g., therapeutic protein). Accordingly, the consistency of cell culture media is increasingly important. Further, media in mammalian cell cultures is a critical raw material (CRM), which may have influence on some of the critical quality attributes (CQA) of a product produced in the cell culture or a product produced using the cell culture.

Media supplemented with serum can be particularly unpredictable, given the undefined nature of animal sera and batch-to-batch variability leading to differences in cell growth and productivity. Further, contaminants may be introduced into the final product and there may be ethical issues involved, particularly in the case of fetal bovine serum (FBS). Accordingly, serum-free media may be desirable. Serum-free media may be composed of cell growth factors including hydrolysates, amino acids, vitamins and inorganic salts. Serum-free media may also contain undefined animal derived products such as serum albumin, hormones, carrier proteins and attachment factors, which may contain contaminants.

In general, media may contain one or more of the following: amino acids, (e.g., about twenty different amino acids), a purine (e.g., hypoxanthine), pyrimidine (e.g., thymidine), choline, inositol, thiamine, folic acid, biotin, calcium, niacinamide, pyridoxine, riboflavin, thymidine, cyanocobalamin, pyruvate, lipoic acid, magnesium, glucose, sodium, potassium, iron, copper, zinc, and sodium bicarbonate. In some cases, the media may contain serum from a mammal. In other cases, the media may be serum-free. The media may contain trace metals, a mammalian growth hormone, and/or a mammalian growth factor.

In some cases, the media, may contain over 100 components. In other cases, the media may be limited to less than 10 components, e.g., inorganic salts, a carbon source, and water. In the latter cases, the cell culture may be maintained in a basal medium with no further supplements.

Serum-free media may be inconsistent because of poorly defined components, such as peptones and hydrolysates, which may be added to simulate the growth achieved with serum containing media. Hydrolysates may be complex mixtures containing oligopeptides, amino acids, iron salts, lipids, vitamins and other low molar mass substances in trace elements, which have been shown to be a suitable replacement for recombinant insulin and serum components in media.

The media may be chemically defined. Accordingly, all of the components are identified with known concentrations. Hence, the chemically defined media may be totally free of animal derived components, such as bovine serum albumin, human serum albumin or fetal bovine serum.

Thus, chemically defined media may be advantageous for controlling the cell culture to produce a target product. However, chemically defined media may have a significant variance with respect to some of the components, especially trace components such as vitamins, amino acids and metals such as zinc, iron, and copper. Further, there may be variance of impurities in chemical compounds such as residues of trace elements.

It may be problematic to provide media limited solely to chemically defined components. Accordingly, chemically defined media may be supplemented with recombinant versions of albumin and/or growth factors. The chemically defined media may include a mix of nutrients and/or a basal formulation. Moreover, the chemically defined medium may be supplemented with poorly defined components, such as hydrolysates. The chemically defined media may also include elements discussed above that meet specified requirements. Such supplemented media may still be serum-free.

The cell culture may be used for producing recombinant proteins with clinical applications. Accordingly, a mammalian cell culture may be suitable. However, other cell cultures may be used.

The media may be provided in liquid or powder form.

Powdered media may be desirable (e.g., more desirable than liquid media) for various reasons. In particular, high transportation cost and limited shelf-life may restrict the applicability of liquid media formulations. For example, some media components (e.g., amino acids) are not chemically stable in liquid form after a few days or weeks. These media components may be more stable (i.e., they may last longer) in powder form. Also, powder may provide flexibility in terms of scaling up or down production processes without large investments for storage of large quantities of unused liquids.

Powdered media may also introduce problems. In particular, powder may have a natural variation based on, e.g., weighing errors, blending and mixing in homogeneity, different humidity levels of the environment, etc.

In view of the above, inconsistencies or variations in media may be a significant (or even the most significant) source of process variation and project rejection, resulting in quality control failure.

In order to detect and adapt to variations in media, analytic techniques may be applied in order to determine the components of the media. The analytical techniques may include separation methods and spectroscopy. The spectroscopy techniques may include near-infrared (NIR), mid-infrared (MIR), Raman, fluorescence, and nuclear magnetic resonance (NMR). Moreover, spectroscopic techniques to quantify trace elements may be applied; such techniques may include atomic emission spectroscopy (AES), laser induced breakdown spectroscopy (LIBS) and x-ray fluorescence (XRF). In addition, mass spectroscopy techniques, such as tandem mass spectroscopy, may be used. Chromatographic methods may be applied. Other techniques could also be used.

The analytic techniques may have disadvantages. For example, chromatographic methods coupled with spectroscopic detection methods may be particularly labor intensive since initial pre-concentration extraction steps followed by pre-column derivatization of the monosaccharides is typically required.

Further, spectroscopic analysis of materials may reveal only partial sample information due to limited sensitivity. Although mass spectroscopy techniques may reveal additional information, these techniques are also limited by the completeness of the reference library used for the identification process. Many spectroscopy techniques, such as infrared or Raman, may have difficulty with low concentrations of components. More sensitive techniques, such as surface enhanced Raman spectroscopy (SERS), might be difficult to implement reproducibly or might not be developed for commercial validation. Some techniques may also be affected by the turbidity of the media.

Moreover, some analytical techniques, such as nuclear magnetic resonant spectroscopy, may have high capital and operational cost as well as significant space requirements.

Accordingly, fully analyzing the media could be challenging.

In addition, providing a full analytical profile of the media may conflict with the policy of the media manufacturer. In particular, many medium manufacturers may maintain the exact composition of the media as a trade secret and might not wish to reveal it.

Further, components of the media may change over time. Specifically, the media may be influenced by decomposition through aging, as well as demixing (unintended separation) during shipment and/or transportation. Demixing may be particularly applicable for powdered media.

Thus, it may be a problem to handle variations in media and adapt control of a cell culture in a production-scale with regard to a starting medium.

According to an aspect, a computer implemented method for adapting control of a cell culture in a production-scale vessel with regard to a starting medium is provided. The method comprises providing multiple production-scale process trajectories, each derived from a successfully controlled cell culture. The method further comprises receiving a media lot for the cell culture. The method further comprises sampling first media from the media lot for possible use in the production-scale vessel. Moreover, the method comprises starting a seed train using the first media to achieve inoculation of the production-scale vessel. The method further comprises providing a plurality of micro-scale vessels in a process control device, wherein the production-scale is greater than the micro-scale. The method further comprises sampling second media from the media lot for the micro-scale vessels, wherein each of the micro-scale vessels receives a representative portion of the media lot. In addition, the method comprises introducing cells from the seed train into the micro-scale vessels to start cell cultures in each of the micro-scale vessels. The method further comprises controlling and monitoring, via the process control device and at least partly in parallel, the cell cultures in each of the micro-scale vessels. The method further comprises determining, during the cell culture run or at the end of the cell culture run for the micro-scale vessels, process trajectories from each one of the micro-scale vessels. Further, the method comprises determining a statistically representative trajectory from the process trajectories of the micro-scale vessels, wherein the statistically representative trajectory represents an impact of the second media on the cell cultures. Moreover, the method comprises determining whether the first media is suitable for controlling the cell culture in the production-scale vessel based on the impact of the second media on the cell cultures. When the first media is determined to be suitable, the method further comprises comparing the statistically representative trajectory to the provided production-scale process trajectories, and controlling the cell culture in the production-scale vessel, using the first media, based on the comparison.

The adapting of control of the cell culture may refer to the selection of process data for controlling the cell culture based on analysis of the media. The process data may include a production-scale process trajectory, a recipe, and set points. In some cases, adapting control of the cell culture may include controlling the cell culture in order to produce a biopharmaceutical product meeting specified criteria (e.g., process outputs having specified values).

The recipe may be a sequence of one or more steps carried out in a defined order to yield the target product. Accordingly, the recipe may provide instructions for carrying out the process.

In some examples, the starting medium may refer to a portion of the media lot. In particular, the starting medium may refer to media used to inoculate the production-scale vessel. In other words, the starting medium may be synonymous with the first media. The media may be a substrate that supplies one or more of the following: nutrients (e.g., as listed above), growth factors, and hormones.

In some examples, the cell culture may refer to a process by which cells are grown under controlled conditions, outside their natural environment. The cells may have been isolated from living tissue. The cells may be maintained under controlled conditions. The cells may be on a surface or artificial substrate or may be free floating in the media.

The media lot may refer to a specified or significant amount of media. For example, in liquid form, the media lot volume may be up to 10,000 liters. In powder form, the media lot may be up to 6500 kg.

The representative portion of the media lot may be obtained according to laboratory sampling techniques. For example, grab sampling may be used.

In some examples, the vessels may be containers or receptacles. The production-scale vessel may be at least one order of magnitude larger or greater than the micro-scale vessel.

Production scale may also be referred to as macro scale, industrial scale or first scale. Micro scale vessel may also be referred to as laboratory scale, experimental scale or second scale. The production scale may correspond to a first order of magnitude and the micro scale may correspond to a second order of magnitude, where the first order of magnitude differs from the second order of magnitude.

The number of micro-scale vessels may be a multiple of two. For example, there may be at least 4, 6, 8, 12, 24 or 48 micro-scale vessels in the process control device.

Inoculation may describe introducing cells into an environment suited to their growth.

In some cases, the final stage of the seed train may be the production-scale vessel. Accordingly, the same vessel from the seed train may be used to inoculate both a next stage of the seed train and the micro-scale vessels of the process control device with a target inoculation density. The target inoculation density may be $2\times10^6$ cells/mL. The seed train is a multi-step process by which a starting number of cells in a first cell culture is expanded into an n−1 cell culture that contains a sufficient number of cells to inoculate the production-scale vessel at an initial cell density of a target density value. The purpose of the seed train is the generation of an adequate number of cells at the appropriate cell density for inoculation of the production-scale vessel. The seed train may offer space for optimization, e.g., choice of optimal points in time for cell passaging from one scale to a larger scale. Further, the seed train may offer choice of inoculation cell density as well as culture volume.

In some examples, cells from any stage of the seed train from the stage after the cryotube (e.g., stage 2) to stage n−1 may be introduced into the micro-scale vessels. In particular, the cryotube might be too small, and it may be useful to obtain information about the starting medium before the production vessel is inoculated.

In particular, cells may be separated from stage n−2 of the seed train so as to run the cell cultures in the micro-scale vessels in parallel to stage n−1 of the seed train. If n is relatively high (e.g., 7 or more) it may be desirable to take cells from a stage before n−1, e.g., n−2 or earlier. Taking cells from an earlier stage may make it easier to separate media influence on the cells from passage influence (i.e., the influence of passing the cells from one stage to the next). Advantageously, the biological behavior of cells in the micro-scale vessels may be more similar to the biological behavior of cells in the corresponding stage of the seed train than it would be if the cells were separated from a different stage.

In some examples, the same container may be used to inoculate both a stage of the seed train and the micro-scale vessels. For example, the vessel used for the n−2 stage of the seed train may be used to inoculate both the micro-scale vessels and the n−1 stage of the seed train.

At least partly in parallel may refer to execution of multiple processes by the process control device at the same time. The processes may be executed entirely in parallel. Alternatively, processes may be staggered, such that processes in one culture station of the process control device are started during execution of processes in vessels of another cell culture station. In particular, the execution of processes within different culture stations of the process control device may be staggered.

In some examples, process trajectories may be determined throughout the cell culture run. The statistically representative trajectory may be determined from the process trajectories at the end of the cell culture run or at a particular point during the cell culture run. The particular point may be chosen based on time, e.g., halfway through the cell culture run, or may be an interval (e.g., ⅕, ⅖, ⅗, or ⅘ of the way through the cell culture run. Alternatively, the particular point may be a stage of a fed-batch process. For example, the fed-batch process may be divided into about four to eight (e.g., five) phases. The phases may include one or more of the following: lag, fast (or exponential) growth, declining growth, stationary and death. More specifically, the fed-batch process may have phases as described in "Modelling of a Fed-Batch Fermentation Process", Ulla Saarela et al., 2003. The process trajectories and the statistically representative trajectory may be determined at the end of any one (or all) of the phases. In addition or alternatively, the process trajectories and the statistically representative trajectory may be determined after a primary nutrient is exhausted or after a specified decrease (e.g., at least 10% or at least 20%) in cell viability is detected.

The statistically representative trajectory may be a mean or median trajectory. The statistically representative trajectory may be determined after eliminating outliers from the process trajectories and/or may include weighing some process trajectories more heavily than others. The processes within the micro-scale vessels may be controlled in such a way as to decouple naturally occurring statistical variations of the processes from variations introduced by the second media. This may be achieved by varying process parameters for each of the micro-scale vessels according to a design of experiments in order to reflect naturally occurring variations in the process parameters. In this way, the statistically representative trajectory represents the impact of the second media on the cell cultures in the micro-scale vessels. Further, because the second media and the first media are both from the same media lot (i.e., both are representative portions of the media lot), the statistically representative trajectory also represents the impact of the first media on the cell culture in the production scale vessel.

When the first media is determined to be unsuitable for controlling the cell culture in the production scale vessel (e.g., a negative impact of the second media on the cell cultures is too great), the media lot may be discarded. Alternatively, it may be possible to document a deviation of the cell culture in the production scale vessel. Documenting a deviation may be possible if the cell culture run for the micro-scale vessels can be classified as successful even though the statistically representative process trajectory is outside control limits. The cell culture run for the micro-scale vessels may be classified as successful based on process outputs (e.g., key performance indicators or critical quality attributes). The control limits may refer to an upper limit and a lower limit of a reference multivariate process chart for the process (discussed in more detail below).

In the following, a number of examples are discussed; the examples may be combined with aspects disclosed in the application, including the aspect described above.

The media lot may consist of powdered media or liquid media. When the media lot consists of powdered media, the sampling (for the first media and/or the second media) may be carried out in consideration of features of the powdered media including:

- a size range of particles of the powdered media,
- shapes of the particles,
- compositional variation of the particles,
- mass of the media lot,
- mass of the sampled media.

When the media lot consists of powdered media, the sampling may be carried out according to Pierre Gy's sampling theory.

The sampling of the media may be carried out according to theory of sampling guidelines for pharmaceutical products. More particularly, the World Health Organization Guidelines (http://apps.who.int/medicinedocs/documents/s21440en/s21440en.pdf) may be used.

The method may further comprise receiving process parameters to be controlled. Controlling and monitoring the cell cultures in the micro-scale vessels may be carried out according to the process parameters to be controlled and corresponding set points. The method may further comprise setting at least one subset of the set points differently for at least a portion of the micro-scale vessels. The subset of set points may be set according to a design of experiments.

Process parameters may also be referred to as process variables. A process parameter may be a condition of the process that can change the process in some way.

The process parameters to be controlled may constrain or regulate the process. The process parameters to be controlled may be set at the beginning of the process and controlled throughout the process in order to control the environment within the micro-scale vessels. Examples include temperature and stirring speed. Process parameters to be measured may be determined from samples of the fluid or via the first process control device. A process parameter may be a process parameter to be controlled, a process parameter to be measured, or both.

The process parameters to be controlled and the process parameters to be measured may each include one or more of the following: dissolved oxygen (DO), dissolved carbon dioxide, pressure, pH, flow rates, temperature, nutrient level, stirring speed, substrate concentration (e.g., glucose, glutamine or other chemically defined Carbon or Nitrogen sources), metabolite concentration (e.g., lactate, ammonia), oxidation reduction potential, turbidity. The flow rates may include carbon dioxide, oxygen and acids/bases. The nutrient level may refer to organic nutrients (e.g., glucose) or inorganic nutrients (e.g., trace minerals). The values of the process parameters may include time series values.

Each set point may be a value for a process parameter that it is desirable to maintain. For example, if a process temperature needs to be kept within a 0.5° K interval from 37° C., then the set point is 37° C. The set points may include basal set points. As an alternative to set points, ranges may also be used. For example, the temperature process parameter may have a corresponding range of 36.5° C. to 37.5° C.

The method may further comprise splitting the micro-scale vessels into culture stations, where in each culture station includes a portion of the micro-scale vessels. Each of the culture stations may include about one third, about one fourth, or about one sixth of the micro-scale vessels. Setting the subset of the set points differently for the portion of the micro-scale vessels may comprise setting the set points for each of the culture stations according to the design of experiments.

The method may further comprise receiving acceptance ranges for each of the process parameters to be controlled. The acceptance ranges may each reflect an acceptable variance for the corresponding process parameter to be controlled. The design of experiments may reflect variances of the process parameters to be controlled within the acceptance ranges. The method may further comprise receiving a reference multivariate process chart that represents the acceptance ranges. Determining whether the first media is suitable for controlling the cell culture may comprise determining whether the statistically representative trajectory is within an upper limit and a lower limit of the reference multivariate process chart.

Each of the acceptance ranges may include a normal operating range. The normal operating ranges may be part of a design space for controlling the cell culture.

In general, a multivariate process chart (e.g., the reference multivariate process chart) may be used to control of the process. The multivariate process chart may be implemented as a control chart, i.e., a process behavior chart. The multivariate process chart may include a process trajectory showing a desired path of development of the process over time, as well as upper and lower limits (i.e., warning or control limits) defined with respect to the trajectory. Values of process parameters from an actual or current process may be determined (e.g., measurements may be taken) and compared with the multivariate process chart in order to ensure that the process will result in production of a usable product, i.e., a product meeting at least one specified (e.g., predetermined) condition. The specified condition may relate to at least one process output or process parameter.

An advantage to using the multivariate process chart to control the process is that an actual trajectory (i.e., a process trajectory for the process being controlled) derived from process parameter values of the process can be compared with the multivariate process chart in order to recognize deviations of the actual trajectory from the trajectory of the multivariate process chart and to correct the deviations as early as possible. The early correction of process deviations, particularly those outside the upper or lower limits of the multivariate process chart, may result in the production of a product meeting the specified condition.

The design space may be determined based on hundreds of small-scale runs of the process. The design space may include a degree of parameter variation that can be tolerated without adversely affecting the outcome of the process.

The cell culture may be controlled according to a process that has been performed a number of times before, e.g., at least 5-10 times before. The described techniques may be particularly useful when a new media lot is received and the characteristics of the new media lot are not known or are only partially known. The process may have been performed a number of times using media from a different media lot. Accordingly, the reference multivariate process chart may be derived from previous successful runs of the process using different media that does not come from the media lot from which the first and second media were sampled.

The process trajectories for each one of the micro-scale vessels may be determined at the end (i.e., finish or completion) of the cell culture run using process data gathered during the cell culture run, process related data and derivatives of the process data or process related data.

The process trajectories may be determined using data driven modelling including deep learning, machine learning and/or multivariate statistical techniques. The multivariate statistical techniques may include principal components analysis (PCA) and/or projections to latent structures (PLS).

The method may further comprise, when the statistically representative trajectory exceeds the upper limit or the lower limit of the reference multivariate process chart, determining that the first media is not suitable for the production-scale vessel. When the statistically representative trajectory does not exceed the upper limit or the lower limit of the reference multivariate process chart, the method may further comprise determining that the first media is suitable for the production-scale vessel.

Comparing the statistically representative trajectory to the provided production-scale process trajectories may comprise calculating a similarity of the trajectories, wherein the similarity of the trajectories may be calculated according to a multivariate distance measure. The multivariate distance measure may include, but is not limited to, one or more of the following: a Euclidean distance, a Mahalanobis distance, a Hotellings T2 statistic, a Q statistic, a distance to model (DModX) statistic.

The method may further comprise determining, based on the comparison, a production-scale process trajectory most similar to the statistically representative trajectory. The production-scale process trajectory may be determined from the multiple production-scale process trajectories. Controlling the cell culture in the production-scale vessel based on the comparison may comprise controlling the cell culture using the production-scale process trajectory.

Accordingly, an adapted control loop for variations in the starting medium is formed without needing a full analytical profile (i.e., an analysis indicating all of the components) of the starting medium. In particular, the control of the cell culture in the production-scale vessel is adapted according to impact factors of the starting medium determined by monitoring the starting medium and its effect on cell cultures in the micro-scale vessels.

Controlling and monitoring the cell cultures in each of the micro-scale vessels may comprise periodically determining, at least in part by the process control device, process parameter values from the cell cultures in each of the micro-scale vessels. The method may further comprise defining groups within the process parameter values according to a time interval during which the corresponding process parameter values were determined. Each of the groups may include process parameter values determined from multiple ones of the micro-scale vessels.

The time interval may correspond to a duration required for the process control device to obtain a sample of fluid from each one of the micro-scale vessels. The time interval may also correspond to the additional time required to determine process parameter values from the fluid. More particularly, a first group may be defined from process parameter values determined from a first set of samples, including a single sample from each one of the micro-scale vessels.

Further, the groups within (or of) the process parameter values may be defined using a technique for smoothing out localized fluctuations in the process parameter values. More particularly, groups may be defined using a moving average. Accordingly, a first value obtained from a first one of the micro-scale vessels may be excluded from the second group and a second value determined from the first one of the micro-scale vessels may be added. In other words, adjacent groups may be formed by shifting forward, i.e., excluding a first process parameter value determined from one of the micro-scale vessels and including a next value determined from the same one of the micro-scale vessels. Other smoothing techniques could also be applied, e.g., interpolation. In addition, weighting may be applied to more recently obtained values e.g., by giving those values a higher weight, or by giving a lower weight to values that deviate substantially from other process parameter values.

In general, the groups of process parameter values may be defined according to any common characteristic of the process parameter values. The common characteristic (e.g., time interval) reflects a process maturity, i.e., a degree or level of process maturity. In particular, groups may be defined according to similar process maturity. In other words, process parameter values may be grouped according to process maturity (e.g., the time at which the values were determined). In particular, the common characteristic may be one of the following:

- a value of a process output determined from the same micro-scale vessel as the corresponding group of process parameter values. For example, a plurality of process outputs may be periodically determined from the micro-scale vessels. More specifically, a percentage of viable cells may be determined as a process output every six hours from each of the micro-scale vessels. Accordingly, process parameter values determined from micro-scale vessels having a first process output value (e.g., a first percentage of viable cells) may be in a first group, whereas process parameter values determined from micro-scale vessels having a second process output value (e.g., a second percentage of viable cells) may be in a second group. The first process output value may be within a first specified range and the second process output value may be within a second specified range. The first specified range may overlap with the second specified range.
- a range of values for one of the process parameters. For example, the process parameter may be nutrient concentration, and a first group may include process parameter values determined when the nutrient concentration has a specified value. Similarly, a second group of process parameter values may include values determined when the nutrient concentration has a second specified value. The specified values may each be within different, possibly overlapping, ranges of values.

The groups may be defined after sufficient data has been collected from each of the process parameter vessels. For example, the groups may be defined after each of the vessels has been accessed by the process control device.

Defining the groups of process parameter values may include generating a batch evolution model from the process parameter values. Each of the groups may be a subset (e.g., a proper subset) or portion of the process parameter values. The groups of the process parameter values may be defined after the end of the cell culture run for the micro-scale vessels, i.e., after the processes in each of the vessels has been performed until completion and/or all steps in the recipe have been carried out.

Rather than the individual process parameter values, the groups may include multivariate scores derived from the process parameter values, where each of the scores represents multiple process parameter values. The multivariate scores may be determined according to a multivariate statistical process control technique, such as PCA and/or PLS.

Determining the statistically representative trajectory may further comprise determining a mean multivariate process chart from the process trajectories of the micro-scale vessels. The mean multivariate process chart may comprise the statistically representative trajectory, an upper limit for the statistically representative trajectory and a lower limit for the statistically representative trajectory. Determining the statistically representative trajectory may include determining a mean value from each of the groups of process parameter values, establishing the statistically representative trajectory from the mean values and determining the upper limit and the lower limit based on a measure of variation within each group.

The method may further comprise removing outlying process trajectories for the micro-scale vessels before determining the statistically representative trajectory from the process trajectories.

In the context of a batch process, the statistically representative trajectory may be determined according to one of the following approaches.

The statistically representative trajectory may be determined by unfolding process data according to the batch-wise approach (BWU; Batch-Wise Unfolding), that is, to unfold the process trajectories (represented as a three dimensional array) to form a matrix, such that all the information for each batch is contained in one row of the matrix (Nomikos, P., MacGregor, J. F., "Monitoring of batch processes using multi-way principal component analysis", 1994; Nomikos, P., MacGregor, J. F., "Multivariate SPC charts for monitoring batch processes", 1995; and Nomikos, P.; MacGregor, J. F., "Multi-way partial least squares in monitoring batch processes", 1995). Performing data driven modelling on the matrix then summarizes the major sources of variation among the different batches and allows efficient batch-to-batch comparison. This approach also allows for the incorporation of initial conditions (Z) and product quality attributes (Y) associated with each batch when performing data driven modelling.

The statistically representative trajectory may be determined by unfolding process data observation-wise (Observation-Wise Unfolding, OWU), that is, with each row corresponding to an observation at some time in each batch, and each column corresponding to the variables measured (Wold, S. et al., "Modelling and diagnostics of batch processes and analogous kinetic experiments", 1998, Nomikos, "PhD thesis: Statistical control of batch processes", 1994).

Performing data driven modelling (which may include using local batch time or a maturity variable as response variables) on this OWU data leads to a reduced number of variables (so-called model components (T)) that summarize the significant behavior of the process trajectories of the original process variables.

For analysis of differences among batches, the reduced number of model components (T) from the OWU approach may be used, or alternatively, the unfolded OWU data from which the model components were derived. This approach also allows for the incorporation of initial conditions (Z) and product quality attributes (Y) associated with each batch when performing the data driven modelling.

The method may further comprise receiving process parameters to be measured. Monitoring the cell cultures in the micro-scale vessels may comprise determining process parameter values from the process parameters to be measured.

Determining the process parameter values may comprise collecting samples from one or more of the micro-scale vessels and analyzing the samples via one or more scientific instruments. The scientific instruments may include at least one of the following: a molecule identification instrument, a metabolite measuring instrument, a nutrient measuring instrument. The scientific instruments may also be referred to as analysis devices and may be suitable for identifying substances or components of materials to be analyzed (e.g., the cell culture and/or the media). For example, the scientific instruments may include one or more of the following: a spectrometer, a mass spectrometer and a liquid chromatography system (e.g., ultra-high or high performance liquid chromatography system).

The process control device may include one or more sensors for measuring at least one of the following: pH, dissolved oxygen, temperature.

The media may have one or more of the following characteristics: it is chemically defined, it is animal-free and/or serum-free. In particular, the media lot may be chemically defined, animal-free, and/or serum-free.

The cell culture may be a mammalian cell culture, particularly a cell line derived from Chinese hamster ovary cells.

In some examples, the production-scale vessel may be a production bioreactor. More particularly, the production-scale vessel may be a stirred tank reactor (STR) or a rocking motion bioreactor. The production bioreactor may be used in batch, fed-batch or perfusion mode.

Each of the successfully controlled cell cultures may have met at least one success criterion. The success criterion may include at least one process output that meets a specified threshold. Accordingly, the production-scale process trajectories derived from successfully controlled cell cultures may be referred to as golden batch trajectories.

In the context of cells, process outputs may include a total quantity of cells, quantity of cells per unit volume of input fluid, a chemical composition of the cells, amount of cell debris, amount of shear damage or chemical damage, cell viability.

Each of the process outputs is a product quality attribute (e.g., CQA) or a key performance indicator. Process outputs may be distinguished from process parameters in that process parameters can be directly influenced or controlled (e.g., a temperature process parameter may be directly controlled by increasing the temperature in a vessel), whereas process outputs might not be directly controllable. Instead, process outputs may be indirectly influenced by controlling process parameters.

Further details and examples regarding process outputs, key performance indicators and product quality attributes can be found in "Cell culture processes for monoclonal antibody production", Feng Li et al., 2010.

The process outputs may include one or more of the following: a total quantity of product, quantity per unit volume of input fluid or starting material, a specified characteristic, such as the chemical composition of the product, purity of the product, starting material cost, energy cost for the process, glycosylation or glycan profile, charge variants or isoforms, including acidic and basic variants, low molecular weight variants, potency or biological activity, aggregates or aggregation level, fragmentation.

The seed train may have n stages and the final stage of the seed train may be (carried out) in the production-scale vessel. The controlling and monitoring may be carried out in parallel to stage n−1 or n−2 of the seed train.

In some cases, n may be between 6 and 8, such that the seed train has between 6 and 8 stages. Accordingly, a first stage of the seed train may be carried out in a vessel having a volume between about 1 mL and about 2.5 mL. The vessel for carrying out the first stage of the seed train may be a cryogenic tube (i.e., a cryogenic sampling tube) or a shake flask. Accordingly, the first stage may be carried out in a small plastic tube (e.g., a falcon tube) with centrifuged cells and preservative to keep the cells in nitrogen. The preservative may be an dimethyl sulfoxide (DMSO) or glycerol.

The second stage of the seed train may be carried out in a vessel having a volume between about 1 L and about 3 L. The third stage of the seed train may be carried out in a vessel having a volume between about 5 L and about 15 L. The fourth stage of the seed train may be carried out in a vessel having a volume between about 15 L and about 25 L. When stage n−1 is carried out in a vessel having a volume between about 150 L and about 250 L, stage n is carried out in a vessel having a volume between about 400 L and about 600 L. When stage n−1 is carried out in a vessel having a volume between about 400 L and about 600 L, stage n may be carried out in a vessel having a volume between about 800 L and about 1,200 L or between about 1,800 L and about 2,200 L.

Accordingly, stages of the seed train may be carried out in vessels having sizes of 1 mL, 2 L, 10 L, 20 L, 500 L, and 1,000 L. As another example, stages of the seed train may be carried out in vessels having volumes of 2 mL, 2 L, 10 L, 20 L, 1,000 L, 2,000 L. Additional stages between 20 L and 500 L and between 20 L and 1,000 L may be included. In particular, a vessel having a volume of 50 L may also be part of the seed train.

According to another aspect, a computer program may be provided. The computer program comprises instructions that, when the program is executed by a computer, cause the computer to carry out any of the methods described above. The computer program may be embodied in a product. The computer program may be embodied in a computer readable medium. More particularly, the computer program may be tangibly embodied in the computer readable medium.

According to yet another aspect, a system for adapting control of a cell culture in a production-scale vessel with regard to a starting medium is provided. The system comprises a database storing production-scale process trajectories, each derived from a successfully controlled cell culture. The system further comprises a first process control device for controlling the cell culture in the production-scale vessel. The first process control device comprises the production-scale vessel, configured to receive first media from the media lot. The first process control device further comprises a controller operable to receive output from a seed train started using the first media in order to achieve inoculation of the production-scale vessel. The system further comprises a second process control device. The second process control device comprises a plurality of micro-scale vessels, each of the micro-scale vessels being configured to contain a representative portion of the media lot. The production-scale is greater than the micro-scale. The system further comprises a robot capable of addressing each of the vessels, dispensing fluid to each of the vessels, and extracting samples of fluid from each of the vessels. The system further comprises a controller operable to distribute second media sampled from the media lot to the micro-scale vessels, receive cells from the seed train for the micro-scale vessels to start cell cultures in each of the micro-scale vessels. The controller is further operable to control and monitor, at least partly in parallel, the cell cultures in each of the micro-scale vessels. The controller is further operable to determine, at the end of the cell culture run for the micro-scale vessels, process trajectories from each one of the micro-scale vessels. The controller is further operable to determine a statistically representative trajectory from the process trajectories of the micro-scale vessels, wherein the statistically representative trajectory represents an impact of the second media on the cell cultures. The controller is further operable to determine whether the first media is suitable for controlling the cell culture in the production-scale vessel based on the impact of the second media on the cell cultures. When the first media is determined to be suitable, the controller is operable to compare the statistically representative trajectory to the stored production-scale process trajectories and control the cell culture of the production-scale vessel, using the first media, based on the comparison.

According to a further aspect, a use of the system for adapting control of a cell culture in a production-scale vessel with regard to a starting medium is provided.

The subject matter described in this disclosure can be implemented as a method or on a device, possibly in the form of one or more computer programs (e.g., computer program products). Such computer programs may cause a data processing apparatus to perform one or more operations described in the present disclosure.

The subject matter described in the present disclosure can be implemented in a data signal or on a machine readable medium, where the medium is embodied in one or more information carriers, such as a CD-ROM, a DVD-ROM, a semiconductor memory, or a hard disk.

In addition, the subject matter described in the present disclosure can be implemented as a system including a processor, and a memory coupled to the processor. The memory may encode one or more programs to cause the processor to perform one or more of the methods described in the application. Further subject matter described in the present disclosure can be implemented using various machines.

Details of one or more implementations are set forth in the exemplary drawings and description that follow. Other features will be apparent from the description, the drawings, and from the claims.

DETAILED DESCRIPTION

In the following text, a detailed description of examples will be given with reference to the drawings. Various modifications to the examples may be made. In particular, one or more elements of one example may be combined and used in other examples to form new examples.

FIGS. 1 to 5 show parts of a single flow chart, such that each figure includes a portion of the steps for the entire flow chart.

Figure 1:
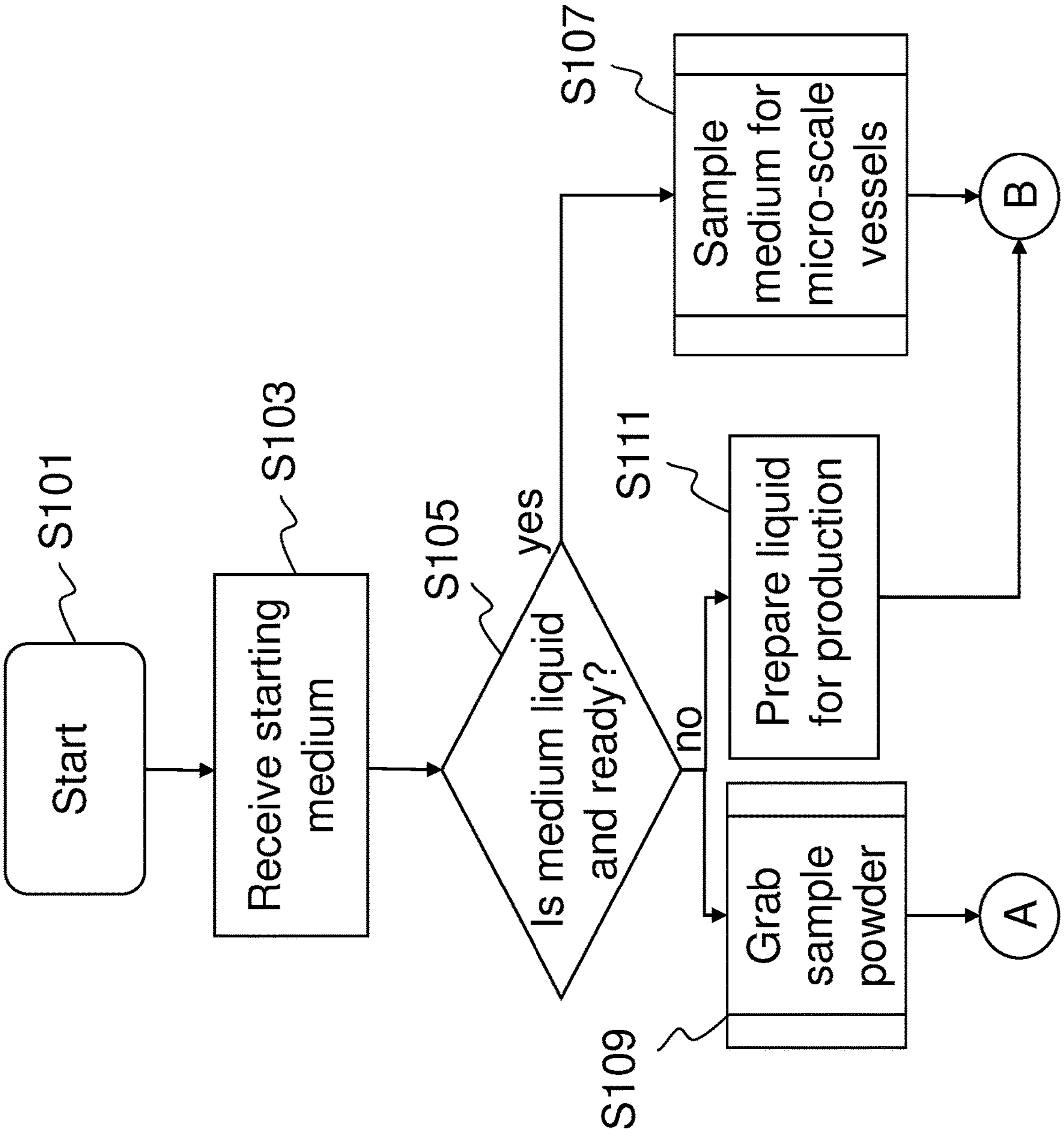
FIG. 1 shows a first part of a flow chart for a method for adapting control of a cell culture in a production-scale vessel with regard to a starting medium.

FIG. 1 begins a method for adapting control of a cell culture in a production-scale vessel with regard to a starting medium at step S101. The cell culture may be controlled during performance of a chemical, pharmaceutical, biopharmaceutical, and/or biological process.

More particularly, the process may be a fed-batch process. Accordingly, the process may have an initial batch phase and a subsequent phase in which constant feeding of a substrate is carried out. In one example, the entire process has a duration of about fourteen days and the initial batch phase lasts about three days.

Adapting control of the cell culture in the production-scale vessel to the staring medium may be desirable for various reasons. For example, there may be a significant degree of variation in components (or amounts of components) between different media lots, even if the media lots are received from the same source. Media lots may be complex mixtures comprising many components, such that it may be prohibitively difficult to identify and quantify every component present in a given media lot. Further, media lot manufacturers may protect the amounts of components, or the components themselves, as a trade secret.

Moreover, it may be difficult to obtain a full analytical profile of a given media lot. Analysis techniques might not provide full information regarding media lot components. In particular, no single spectral technology is capable of capturing all of the relevant information for every media. Further, some analysis techniques (e.g., spectroscopy techniques) may be prohibitively expensive or labor intensive.

At step S103 the starting medium may be received. The starting medium may be from a media lot for the cell culture. The cell culture may be a mammalian cell culture, such as a cell line derived from a Chinese hamster ovary. The media lot may include chemically defined media. The media lot may be serum-free and/or free of animal derived components.

At step S105 it may be determined whether the media is a ready-made liquid. If the media is a ready-made liquid, the media may be sampled at step S107. Samples of the media may be used to start a seed train to achieve inoculation of the production-scale vessel as well as for micro-scale vessels. The liquid media may be mixed so as to ensure that each of the micro-scale vessels receives a representative portion of the media lot.

Figure 6:
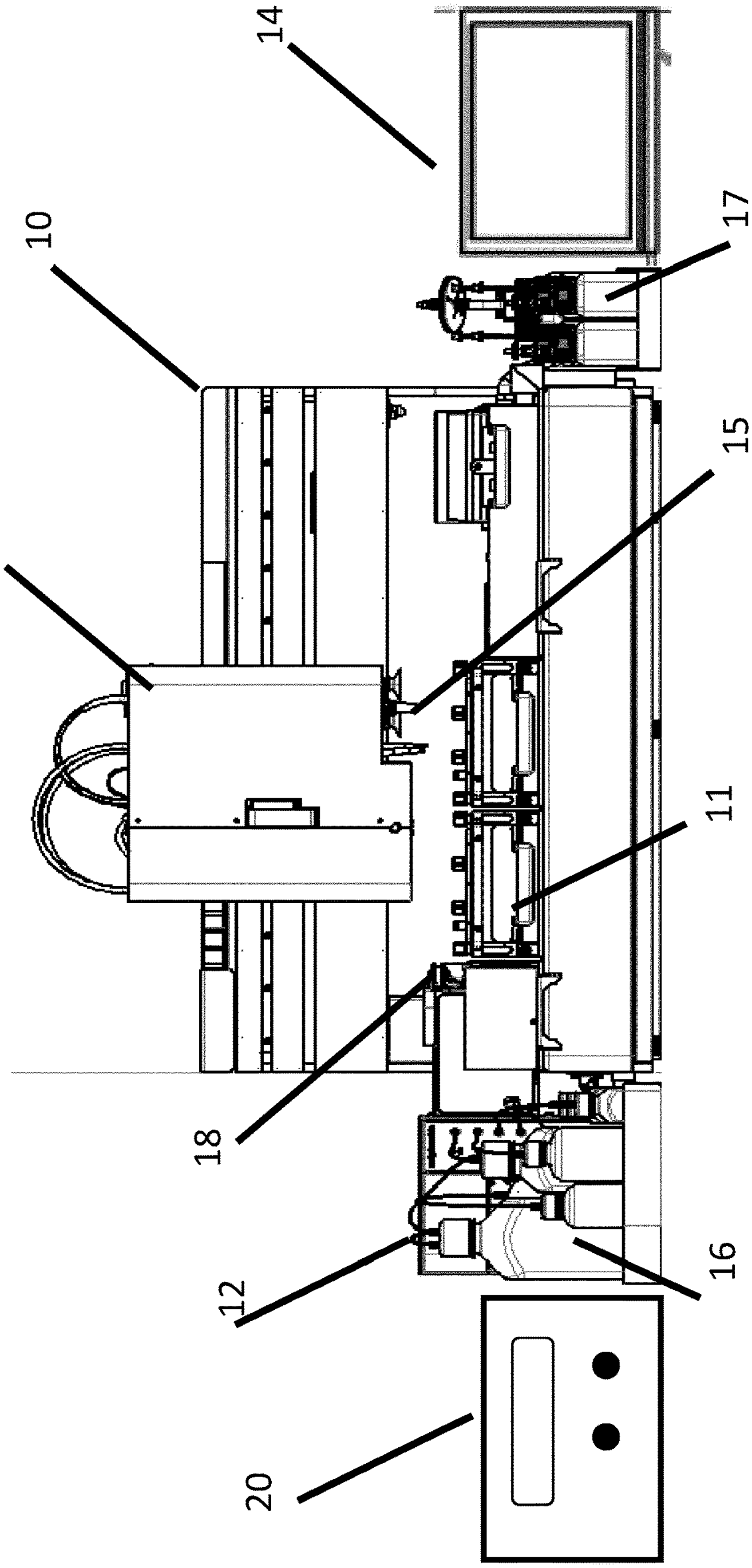
FIG. 6 shows a perspective view of a process control device including a plurality of micro-scale vessels.
Figure 7:
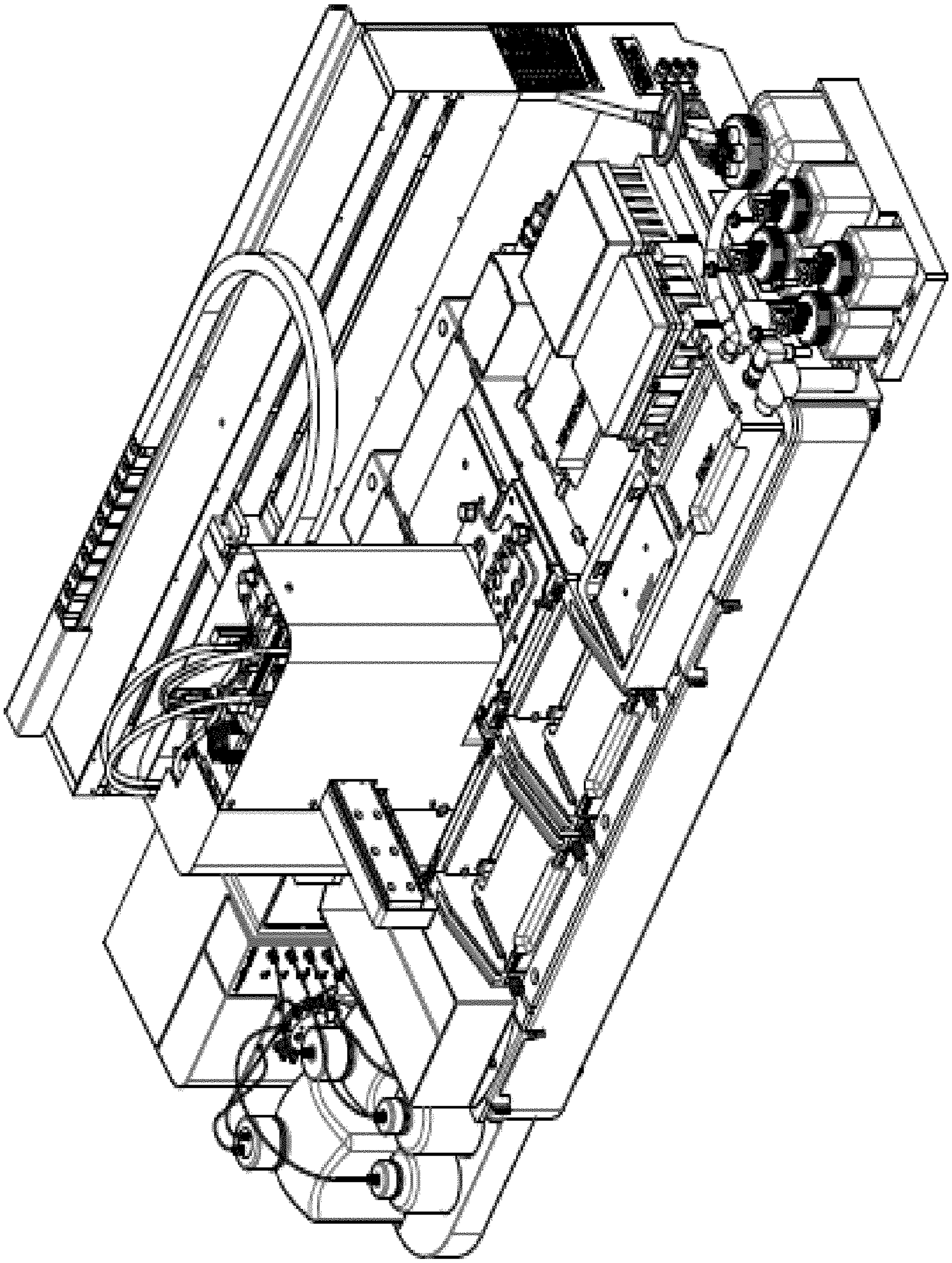
FIG. 7 shows another perspective view of the process control device.

The micro-scale vessels may be provided in a process control device, e.g., as shown in FIGS. 6 and 7.

If the media is not a ready-made liquid, further processing may be required. For example, the media lot may be provided in powder form. If the media lot is provided in powder form, grab sampling may be used to obtain a representative portion of the media lot. If the media is received in liquid form but is not ready for production, the media may be prepared for production at step S111.

Figure 2:
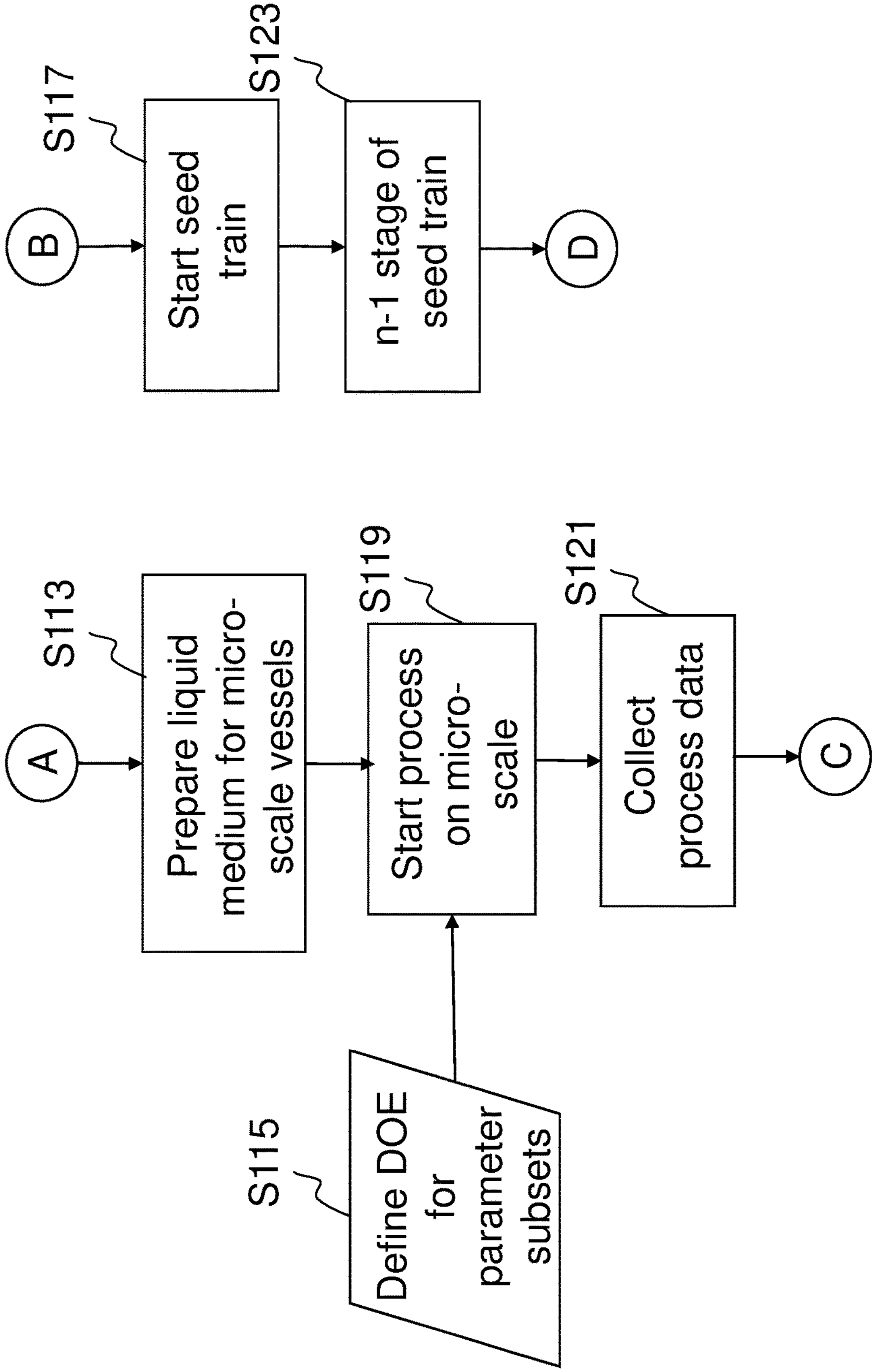
FIG. 2 shows a second part of the flow chart for adapting control of a cell culture in a production-scale vessel with regard to a starting medium.

In FIG. 2, step S113 may directly follow step S109. Step S117 may directly follow either step S107 or step S111.

At step S113, liquid medium for the micro-scale vessels may be prepared from the powder medium discussed in step S109. The liquid medium may be prepared according to conventional techniques.

At step S115, a design of experiments may be defined. The design of experiments may be determined according to values that have been developed during a process development phase, e.g., with a different media lot. The process parameters to be measured and process parameters to be controlled may be received or determined during process development. Further, the process development phase may have been carried out to define a design space, particularly for critical process parameters in order to arrive at critical quality attributes having desired values. Normal operating ranges for each of the process parameters may be defined during process development.

Accordingly, the design of experiments may be defined within the design space, such that naturally occurring variances within the normal operating ranges for each process parameter are reflected in the design of experiments. For example, temperature may vary ±0.1° C. and pH may be defined to vary by ±0.1. Variances may be defined for other process parameters as well.

The micro-scale vessels of the process control device may be divided among different culture stations. For example, when the process control device includes 24 vessels, each of the culture stations may include six of the vessels. Accordingly, each of the culture stations may be configured with different set points. For example, a temperature for the first set of culture stations may be set 0.1° C. degrees lower than the temperature set for the second set of culture stations.

At step S117, a seed train may be started in order to achieve inoculation of the production-scale vessel. The seed train may be started using first media sampled from the media lot. The seed train may go from less than the micro-scale (e.g., a shaking flask or a cryotube) to the production-scale vessel (e.g., a 2,000 L production bioreactor). Stages of the seed train may be carried out in parallel to processing in the micro-scale vessels.

The seed train may be used to inoculate the production-scale vessel at an initial cell density of at least an inoculation threshold amount. In this context, cell density may refer to viable cell density.

Cells in a vessel of the first stage of the seed train may have a cell density of an initial threshold amount. The initial threshold amount may be at least $2\times10^5$ cells/mL. In some cases (depending on the process and/or the cell line), the initial threshold amount may be at least $3\times10^6$ c/mL and up to $10\times10^6$ c/mL.

The production vessel may be inoculated with cells having a cell density of at least an inoculation threshold amount. The inoculation threshold amount may be at least $2\times10^6$ c/mL (cells per milliliter). Depending on the process and/or the cell line, the inoculation threshold amount may be up to $75\times10^6$ or up to $100\times10^6$ cells/mL. In some cases, the n−1 stage of the seed train may have a cell density in the range from 10 to $150\times10^6$ c/mL.

The production-scale vessel may be a (continuous) stirred tank reactor and/or a perfusion bioreactor. The production-scale vessel may also be implemented as a rocking platform or rocking motion vessel. Vessels within the seed train may be implemented as stirred tank reactors, single use bioreactors, perfusion bioreactors, rocking motion reactors. Other implementations or combinations are also possible.

At step S119, cells from the seed train may be introduced into the micro-scale vessels to start cell cultures in the micro-scale vessels. In particular, cells may be separated from the seed train, multiplied with the target and used to inoculate a number of the micro-scale vessels in parallel in order to start a parallel run of the micro-scale vessels so that the micro-scale vessels can be controlled and monitored in parallel to the n−2 or n−1 stage of the seed train. Accordingly, any stage from the second stage to the n−1 stage of the seed train may provide a source of cells that can be used to inoculate the micro-scale vessels. In some cases, it may be desirable to control and monitor the cell cultures in the micro-scale vessels in parallel to either the n−1 or n−2 stages of the seed train.

In some examples, the same media lot from which samples are taken for the seed train, including the production-scale vessel, may also be a source of media for the micro-scale vessels.

At step S121, the cell cultures in each of the micro-scale vessels may be controlled and monitored via the process control device. Accordingly, process data may be collected from the micro-scale vessels. Further, scientific instruments (e.g., instruments capable of spectroscopic measurements) as well as inline sensors (e.g., pH, dissolved oxygen, biomass) and attached online of offline analysis of process parameters, process key performance indicators and critical quality attributes may be performed. Multivariate analysis may be carried out in order to derive conclusions from the process data.

Process parameter values may be collected for at least the following process parameters: pH, temperature, dissolved oxygen, stirring speed, gassing rate. Online process parameter values may include values for the following process parameters: oxygen, carbon dioxide. Atline process parameter values may include values for nutrients such as glucose and lactose. Offline data (e.g., data collected using a scientific instrument such as a spectrometer) may include glucose, ammonia, titers, ammonia acids, nicotinamide adenine dinucleotide (NADH). Multivariate data may also be determined, e.g., from principal components derived from values of multiple process parameters.

At step S123, stage n−1 of the seed train may be reached. Stage n−1 may be a 500 L vessel or a 200 L vessel. Other vessel sizes are also possible. Stage n−1 may be the stage just before the production-scale vessel. Accordingly, the size of the vessel used at stage n−1 of the seed train may be about half the size of the production-scale vessel.

Process data may include values of process parameters determined during the course of the process. The determined process parameter values may be derived from process parameters to be measured (e.g., measured temperature or pH) or may be determined via analysis (e.g., spectroscopically) or may be determined via a hybrid system model (e.g. metabolic rates). A hybrid system model is where experimentally measured data is combined with theoretical process models (e.g. metabolic flux balance analysis) to create different state observers (e.g. metabolic state observer).

Figure 3:
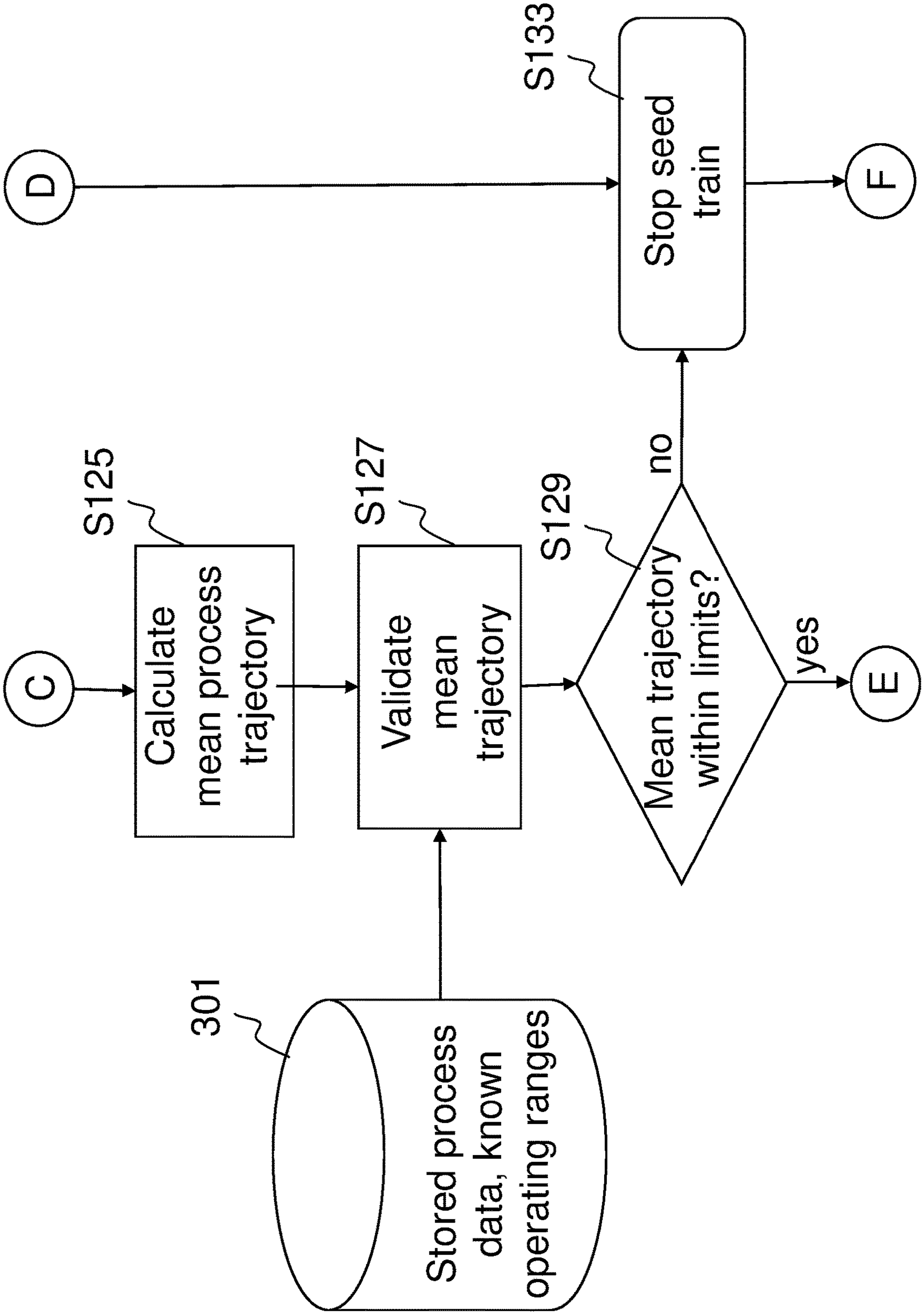
FIG. 3 shows a third part of the flow chart for adapting control of a cell culture in a production-scale vessel with regard to a starting medium.

FIG. 3 includes steps S125 to S133. Step S125 follows directly after step S121. Step S133 directly follows step S123.

At step S125, a statistically representative trajectory may be determined from the process trajectories of the micro-scale vessels. The process trajectories from the micro-scale vessels may be determined at the end of the cell culture run for the micro-scale vessels. The end of the cell culture run may occur:

- after a specified amount of time has elapsed,
- after certain process outputs are measured or determined from the process, or
- after multivariate analysis of process parameter values and/or quality attributes arrives at a specified result.

The end of the cell culture run may refer to a finish or completion of the process.

The statistically representative trajectory may be a mean of the process trajectories from the micro-scale vessels, e.g., after outliers have been removed. The process trajectories may also be referred to as process data trajectories. Alternatively, the statistically representative trajectory may be determined by defining groups within process parameter values determined from the cell cultures in each of the micro-scale vessels. The groups of process parameter values may be defined according to a time interval during which those values were determined. Each of the groups of process parameter values may be determined from multiple ones of the micro-scale vessels.

At step S127, the statistically representative process trajectory may be validated using stored process data from a database 301. The stored process data may include acceptance ranges (e.g., reference trajectories and known operating ranges) for each of the process parameters. The stored process data may have been obtained during process development for the process, e.g., using media from other media lots. The validation may include determining whether the statistically representative process trajectory is within acceptance ranges represented by a reference multivariate process chart (e.g., whether the statistically representative process trajectory is within upper and lower limits of the multivariate process chart).

At step S129, it may be determined whether the statistically representative trajectory exceeds an upper limit or a lower limit or limit of the reference multivariate process chart. If the statistically representative trajectory is within the limits of the reference multivariate process chart, the media may be determined to be suitable for controlling the cell culture in the production-scale vessel.

Step S133 may be carried out after step S129. Accordingly, the process may be continued as shown in FIG. 4.

Alternatively, when the statistically representative trajectory is not within the limits of the reference multivariate process chart, the seed train may be stopped at step S133. The determination that the statistically representative trajectory is not within the limits of the reference multivariate process chart may be a sufficient indication that the media is not suitable for use in the production-scale vessel. Accordingly, the process may be stopped at step S133. Alternatively, additional analysis may be carried out in order to determine how to adapt control of a cell culture in a production-scale vessel with regard to a starting medium.

Figure 4:
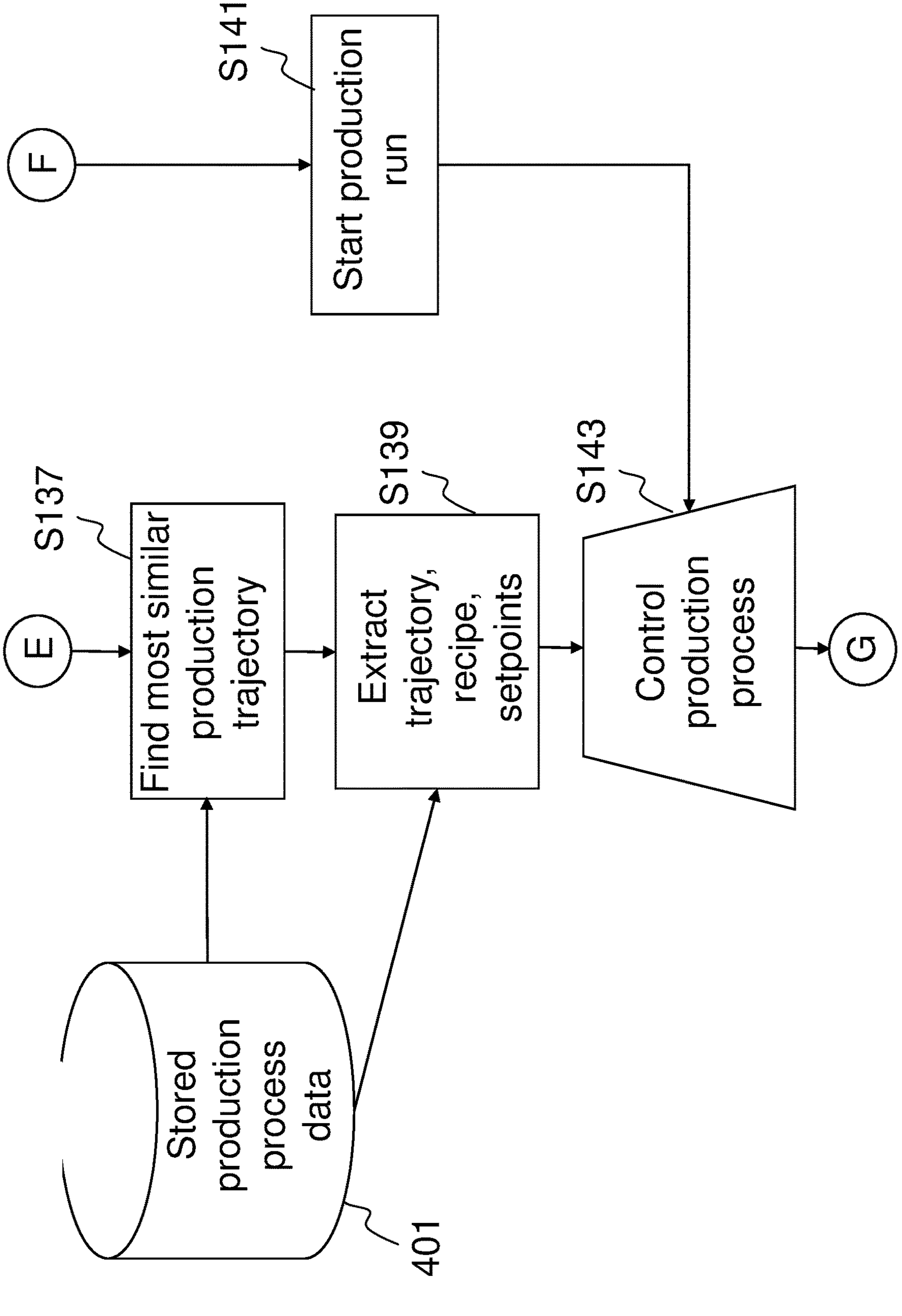
FIG. 4 shows a fourth part of the flow chart for adapting control of a cell culture in a production-scale vessel with regard to a starting medium.

If a way forward can be found via further analysis, the process may be continued with step S141 of FIG. 4.

FIG. 4 shows a database 401 for stored production process data. The database 401 may be part of the database 301. Alternatively, the database 401 may be implemented as a separate database. Step S137 may be carried out when the first media is determined to be suitable for controlling the cell culture in the production-scale vessel in view of the impact of the second media on the cell culture in the production scale vessel. Step S137 may include finding a production-scale process trajectory that is most similar to the statistically representative trajectory. Accordingly, step S137 may be carried out by searching the database 401 and comparing trajectories for production processes stored in the database 401 with the statistically representative trajectory. The comparison of trajectories may be carried out using a multivariate distance measure. The multivariate distance measure may include one or more of the following: Euclidean distance, a Hotellings T2 range, a distance to model (e.g., DModX), a Mahalanobis distance. Other techniques may also be used.

The production (i.e., production-scale) process trajectory most similar to the statistically representative trajectory may be extracted from the database at step S139. In addition, a recipe and corresponding set points may be associated with the production process trajectory in the database 401 and may be extracted along with the production process trajectory.

At step S141, the final stage of the seed train may be started. Accordingly, the cell culture may be started in the production-scale vessel. At step S143, the cell culture in the production-scale vessel may be controlled and monitored. The cell culture in the production-scale vessel may be cultivated using the first media. The cell culture in the production-scale vessel may be controlled and monitored based on the comparison of the statistically representative trajectory to the production-scale process trajectories in the database 401. In particular, the cell culture in the production-scale vessel may be controlled and monitored using the trajectory stored in the database 401 that is most similar to the statistically representative trajectory. The database 401 may include a number of production process trajectories, possibly from multiple users. In particular, the database 401 may include at least 5 production process trajectories, at least 10 production process trajectories, or at least 20 production process trajectories.

Figure 5:
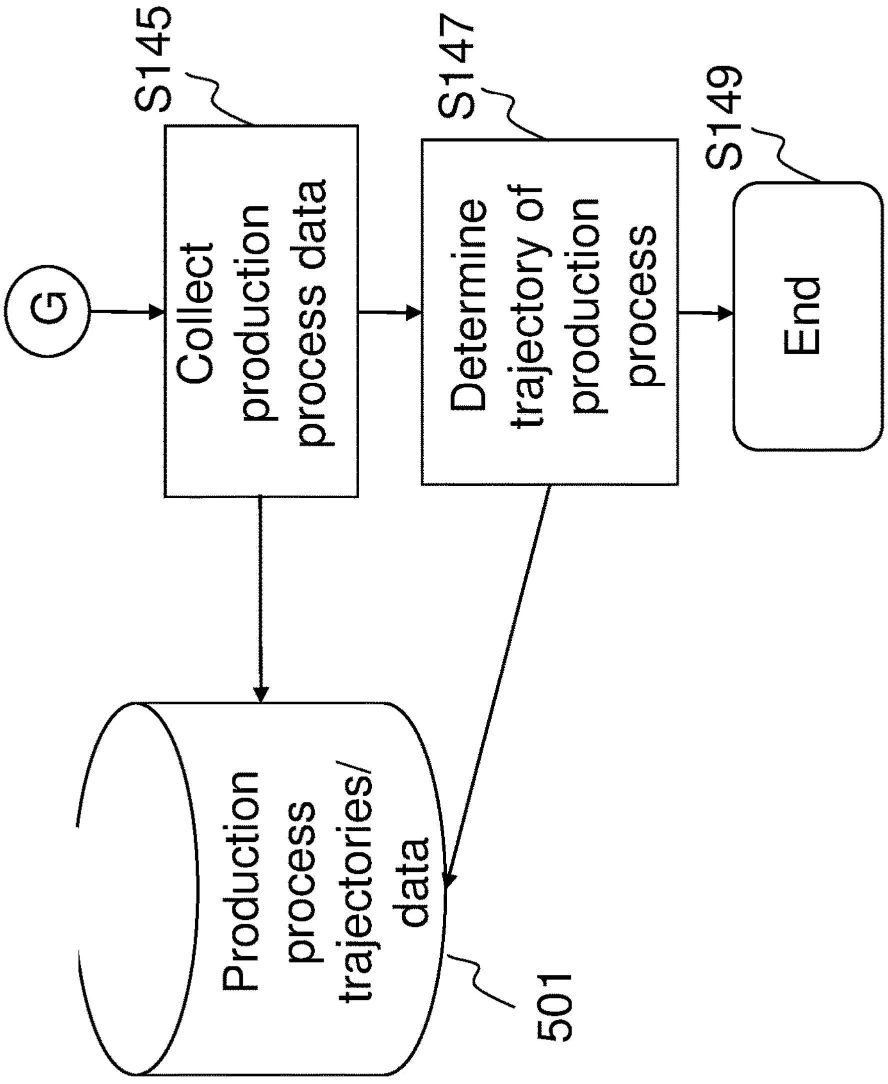
FIG. 5 shows a fifth part of the flow chart for adapting control of a cell culture in a production-scale vessel with regard to a starting medium.

Continuing the process in FIG. 5, process data may be collected from the production process at step S105. Process data may be collected while controlling and monitoring the production process. The process data collected at step S145 may be stored in a database 501. Further, the recipe and set points extracted from the database 401 may be modified at step S145 and stored in the database 501. The database 501 may be separate from or part of the database 401. In particular, the databases 301, 401, and 501 may be separate databases (e.g., on separate computer systems) or may be implemented as a single database having multiple tables. At step S147, a trajectory of the production process may be determined. The trajectory may be developed during the course of the production process and may be finally determined after the production process ends. The determined trajectory of the production process may be stored in the database 501. In addition to this trajectory, an updated recipe as well as updated set points may be stored for the production process. An association between the production process trajectory, the updated set points, and the updated recipe may be created within the database 501.

At step S149, the process ends.

A process control device 10 (possibly implemented as a bioreactor system) including an array of vessels (e.g., micro-scale bioreactors) is shown in FIG. 6. The vessels are configured to contain fluid for producing a biopharmaceutical product (other types of fluid are also possible) from a cell culture. The process control device 10 may correspond to the process control device discussed above. The vessels may be located in a vessel station 11 (also referred to as a receiving station). The vessel station 11 is configured to receive a specified number of vessels, e.g., 6, 12 or 24. The process control device 10 is operable to control and/or monitor the vessels in the vessel station 11 at least partly in parallel, possibly entirely in parallel. The process control device 10 is operable to determine or set process parameters to be controlled (i.e., process control parameters). Examples of process parameters to be controlled include stirring speed and rate of gas supply.

The process control device 10 is operable to cause process parameter values to be periodically determined for process parameters (e.g., process parameters to be measured). The process parameter values may be determined directly from the vessels (e.g., via sensor spots) or from samples taken from the vessels. More particularly, the analysis module 12 may be used to process fluid (e.g., samples) from the vessels in order to determine process parameter values. Accordingly, the analysis module 12 may route fluid from the vessels to a scientific instrument (e.g., analysis instrument) to determine values for process parameters such as pH, cell count, metabolite level, nutrient level. pH values determine via the analysis module may be used for sensor calibration. The analysis module 12 may also support preparation of samples as well as cleaning and flushing after collecting samples.

The process control device 10 includes a robot, possibly implemented as a liquid handler 13. The robot is capable of addressing each first scale vessel, as well as dispensing and extracting fluid from the vessels. The liquid handler 13 performs automated process control and sampling. The liquid hander 13 collects (or draws) samples from each individual vessel in the vessel station 11 and feeds nutrients or detergent (e.g., acid, base, antifoam, etc.) to each individual vessel. These tasks may also be performed by the robot in implementations than the liquid handler 13.

The process control device 10 may include a process control module 14 (also referred to as a workstation). The process control module 14 includes a user interface (e.g., input device(s) such as a keyboard, output device(s) such as a display, processing means, storage). The process control module may store a process control strategy to control the process control device 10, more specifically, to control the liquid handler 13 and the analysis module 12. In particular, the process control device may store values for process parameters to be controlled (i.e., control set points). Further, the process control device may store a recipe for the process.

The process control device 10 may include a sampling device 15. More specifically, the liquid handler 13 may include the sampling device 15. The sampling device 15 may implement an automated pipetting system and/or carry pipet tips.

The process control device 10 may include liquids 16 to supply to the analysis module 12. The liquids 16 may include cleaning and rinsing agents, pH buffers, calibration solutions, etc.

The analysis module 12 and the process control module 14 may be combined in a controller.

Storage containers 17 may be used to store liquids to be supplied to the vessels. The liquids from the storage containers 17 may be supplied by the process control device 10, particularly the liquid handler 13. The liquids may include glucose feed, acids, bases, antifoam solution, etc.

The process control device 10 may include a sample holder or receptacle, possibly implemented as sample cup 18. More particularly, the sample cup 18 may be part of the analysis module 12. The sample cup 18 may be configured to receive a sample taken by the liquid handler 13 and/or the sampling device 15, and to feed the sample to the analysis module 12 as well as to further analytical devices.

The process control device 10 may include a scientific instrument, possibly in the form of analytical device 20. The analytical device 20 may be implemented as a Raman measurement system (i.e., spectrometer), a high performance liquid chromatography (HPLC) device, or a mass spectrometry device. There may be multiple analytical devices (not shown). The analytical device 20 may be configured to receive samples from the analysis module 12 and perform analytical measurements to determine process parameter values or process outputs. The process outputs may include product quality attributes, such as glycosylation.

One or more heaters or chillers (not shown) may be located adjacent to the vessel station 11 to control the temperature of the vessels.

FIG. 7 shows the process control device of FIG. 6 from an overhead perspective.

The invention claimed is:

1. A computer-implemented method for adapting control of a cell culture in a production-scale vessel with regard to a starting medium, comprising:
- providing multiple production-scale process trajectories, each derived from a successfully controlled cell culture;
- receiving a media lot for the cell culture;
- sampling first media from the media lot for possible use in the production-scale vessel;
- starting a seed train using the first media to achieve inoculation of the production-scale vessel;
- providing a plurality of micro-scale vessels in a process-control device, wherein the production-scale is greater than the micro-scale;
- sampling second media from the media lot for the micro-scale vessels, wherein each of the micro-scale vessels receives a representative portion of the media lot;
- introducing cells from the seed train into the micro-scale vessels to start cell cultures in each of the micro-scale vessels;
- controlling and monitoring, via the process-control device and at least partly in parallel, the cell cultures in each of the micro-scale vessels;
- determining, during the cell culture run or at the end of the cell culture run for the micro-scale vessels, process trajectories from each one of the micro-scale vessels;
- determining a statistically representative trajectory from the process trajectories of the microscale vessels, wherein the statistically representative trajectory represents an impact of the second media on the cell cultures;
- determining whether the first media is suitable for controlling the cell culture in the production-scale vessel based on the impact of the second media on the cell cultures; and
- after determining that the first media is suitable:
  - comparing the statistically representative trajectory to the provided production-scale process trajectories; and
  - controlling the cell culture in the production-scale vessel, using the first media, based on the comparison, wherein the comparing comprises calculating a similarity of the trajectories, wherein the similarity of the trajectories is calculated according to a multivariate distance measure.

2. The method of claim 1, wherein the media lot consists of powdered media or liquid media, and wherein when the media lot consists of powdered media, the sampling is carried out in consideration of features of the powdered media including:

a size range of particles of the powdered media, shapes of the particles, compositional variation of the particles, mass of the media lot, or mass of the sampled media.

3. The method of claim 2, wherein the media lot consists of powdered media and the sampling is carried out according to Pierre Gy's sampling theory.

4. The method of claim 1, further comprising:

receiving process parameters to be controlled, wherein controlling and monitoring the cell cultures in the micro-scale vessels is carried out according to the process parameters to be controlled and corresponding set points; and setting at least one subset of the set points differently for at least a portion of the micro-scale vessels, wherein the subset of set points is set according to a design of experiments.

5. The method of claim 4, further comprising:

splitting the micro-scale vessels into culture stations, wherein each culture station includes a portion of the micro-scale vessels, wherein each of the culture stations includes about one third, about one fourth, or about one sixth of the micro-scale vessels;

wherein setting the subset of the set points differently for the portion of micro-scale vessels comprises setting the set points for each of the culture stations according to the design of experiments.

6. The method of claim 4, further comprising:

receiving acceptance ranges for each of the process parameters to be controlled; and receiving a reference multivariate process chart that represents the acceptance ranges, wherein the acceptance ranges each reflect an acceptable variance for the corresponding process parameter to be controlled, wherein the design of experiments reflects variances of the process parameters to be controlled within the acceptance ranges, and wherein determining whether the first media is suitable for controlling the cell culture comprises determining whether the statistically representative trajectory is within an upper limit and a lower limit of the reference multivariate process chart.

7. The method of claim 6, further comprising:

when the statistically representative trajectory exceeds the upper limit or the lower limit of the reference multivariate process chart, determining that the first media is not suitable for the production-scale vessel; and when the statistically representative trajectory does not exceed the upper limit or the lower limit of the reference multivariate process chart, determining that the first media is suitable for the production-scale vessel.

8. The method of claim 1, further comprising:

determining, based on the comparison, a production-scale process trajectory most similar to the statistically representative trajectory, wherein controlling the cell culture in the production-scale vessel based on the comparison comprises controlling the cell culture using the production-scale process trajectory.

9. The method of claim 1, wherein controlling and monitoring the cell cultures in each of the micro-scale vessels comprises:

periodically determining, at least in part by the process-control device, process parameter values from the cell cultures in each of the micro-scale vessels; and defining groups within the process parameter values according to a time interval during which the corresponding process parameter values were determined, wherein each of the groups includes process parameter values determined from multiple ones of the micro-scale vessels.

10. The method of claim 9, wherein determining the statistically representative trajectory further comprises:

determining a mean multivariate process chart from the process trajectories of the micro-scale vessels, the mean multivariate process chart comprising:

the statistically representative trajectory, an upper limit for the statistically representative trajectory and a lower limit for the statistically representative trajectory, including:

determining a mean value from each of the groups of process parameter values;

establishing the statistically representative trajectory from the mean values; and determining the upper limit and the lower limit based on a measure of variation within each group.

11. The method of claim 1, further comprising: receiving process parameters to be measured, wherein monitoring the cell cultures in the micro-scale vessels comprises determining process parameter values for the process parameters to be measured, comprising:

collecting samples from one or more of the micro-scale vessels; and analyzing the samples, wherein analyzing the samples comprises measuring concentrations of metabolites and/or nutrients.

12. The method of claim 1, wherein the media has one or more of the following characteristics:

it is chemically defined;

it is animal-free and/or serum-free.

13. The method of claim 1, wherein the seed train has n stages, wherein the final stage of the seed train is in the production-scale vessel, and wherein the controlling and monitoring are is carried out in parallel to stage n−2 or n−1 of the seed train.

14. The method of claim 1, wherein the seed train has n stages, wherein n is between six and eight, wherein a first stage is carried out in a vessel having a volume between about 1 ml and about 2.5 ml, wherein the vessel for carrying out the first stage is a cryogenic tube or a shake flask, wherein a second stage is carried out in a vessel having a volume between about 1 L and about 3 L, wherein a third stage is carried out in a vessel having a volume between about 5 L and about 15 L, wherein a fourth stage is carried out in a vessel having a volume between about 15 L and about 25 L, when stage n−1 is carried out in a vessel having a volume between about 150 L and about 250 L, stage n is carried out in a vessel having a volume between about 400 L and about 600 L, and when stage n−1 is carried out in a vessel having a volume between about 400 L and about 600 L, stage n is carried out in a vessel having a volume between about 800 L and about 1200 L or between about 1800 L and about 2200 L.

15. The method of claim 1, wherein the multivariate distance measure includes one or more selected from the following:

a Euclidean distance, a Hotellings T2 range, a distance to model (DModX), and a Mahalanobis distance.

16. A system for adapting control of a cell culture in a production-scale vessel with regard to a starting medium, the system comprising:

a database storing production-scale process trajectories, each derived from a successfully controlled cell culture;

a first process-control device for controlling the cell culture in the production-scale vessel, the first process-control device comprising:

the production-scale vessel, configured to receive first media from a media lot;

a first controller operable to receive output from a seed train started using the first media in order to achieve inoculation of the production-scale vessel;

a second process-control device, the second process-control device comprising:

a plurality of micro-scale vessels, each of the micro-scale vessels being configured to contain a representative portion of the media lot, wherein the production-scale is greater than the micro-scale;

a robot capable of addressing each of the vessels, dispensing fluid to each of the vessels, and extracting samples of fluid from each of the vessels; and a second controller comprising a processor and a non-transitory data storage device storing instructions that, when executed by the processor, cause the second controller to:

distribute second media sampled from the media lot to the micro-scale vessels;

receive cells from the seed train for the micro-scale vessels to start cell cultures in each of the micro-scale vessels;

control and monitor, at least partly in parallel, the cell cultures in each of the micro-scale vessels;

determine, during the cell culture run or at the end of the cell culture run for the micro-scale vessels, process trajectories from each one of the micro-scale vessels;

determine a statistically representative trajectory from the process trajectories of the micro-scale vessels, wherein the statistically representative trajectory represents an impact of the second media on the cell cultures;

determine whether the first media is suitable for controlling the cell culture in the production-scale vessel based on the impact of the second media on the cell cultures; and after determining that the first media is suitable:

compare the statistically representative trajectory to the stored production-scale process trajectories; and control the cell culture of the production-scale vessel, using the first media, based on the comparison, wherein the comparing comprises calculating a similarity of the trajectories, wherein the similarity of the trajectories is calculated according to a multivariate distance measure.

17. The system of claim 16, wherein the multivariate distance measure includes one or more selected from the following:

a Euclidean distance, a Hotellings T2 range, a distance to model (DModX), and a Mahalanobis distance.

* * * * *